United States Patent
Barton et al.

(10) Patent No.: US 6,814,706 B2
(45) Date of Patent: Nov. 9, 2004

(54) SKIN PATCH INCLUDING A TEMPERATURE SENSOR

(75) Inventors: Donna K. Barton, Bend, OR (US); Florian G. Bell, Bend, OR (US); Jesse S. Laird, Bend, OR (US); Thomas Clifton Meyer, Bend, OR (US)

(73) Assignee: Mini Mitter Co., Inc., Bend, OR (US)

( * ) Notice: Subject to any disclaimer, the term of this patent is extended or adjusted under 35 U.S.C. 154(b) by 269 days.

(21) Appl. No.: 10/071,534

(22) Filed: Feb. 8, 2002

(65) Prior Publication Data

US 2002/0107436 A1 Aug. 8, 2002

Related U.S. Application Data

(60) Provisional application No. 60/267,593, filed on Feb. 8, 2001.

(51) Int. Cl.$^7$ ................................. A61B 5/00
(52) U.S. Cl. ................. 600/549; 600/300; 600/481; 600/544; 600/546; 128/903
(58) Field of Search ............... 600/300, 301, 600/306, 307, 362, 372, 382, 386, 391, 392, 481, 485, 508, 509, 544, 546, 549, 587; 128/903; 340/870.05, 870.17, 870.19, 870.24, 870.37, 539, 855.4; 374/170, 183

(56) References Cited

U.S. PATENT DOCUMENTS

| | | | | |
|---|---|---|---|---|
| 5,255,979 A | * | 10/1993 | Ferrari | 374/158 |
| 6,113,539 A | * | 9/2000 | Ridenour | 600/300 |
| 6,315,719 B1 | * | 11/2001 | Rode et al. | 600/300 |
| 6,385,473 B1 | * | 5/2002 | Haines et al. | 600/393 |
| 6,572,636 B1 | * | 6/2003 | Hagen et al. | 600/500 |
| 6,611,783 B2 | * | 8/2003 | Kelly et al. | 702/150 |
| 6,629,776 B2 | * | 10/2003 | Bell et al. | 374/170 |
| 6,643,541 B2 | * | 11/2003 | Mok et al. | 600/546 |
| 2002/0075163 A1 | * | 6/2002 | Smith et al. | 340/870.16 |

OTHER PUBLICATIONS

Ferrell, T.L.; P.B. Crilly; S.F. Smith; A.L. Wintenberg; C.L. Britton; G.W. Morrison; M.N. Ericson; D. Hedden; D. Houldin; A. Passian; T. Downey, A. Wig; and F. Meriaudeau, "Medical Telesensors"; *SPIE*, vol. 3253, 0277–7876X/98; publication date unknown.

* cited by examiner

Primary Examiner—Charles Marmor
(74) Attorney, Agent, or Firm—John Smith Hill; Smith-Hill and Bedell

(57) ABSTRACT

A skin patch includes first and second layers of material and a telesensor sandwiched between the first and second layers. The first layer has a coating of skin-compatible adhesive material on its face that is remote from the second layer.

23 Claims, 1 Drawing Sheet

SKIN PATCH INCLUDING A TEMPERATURE SENSOR

CROSS-REFERENCE TO RELATED APPLICATION

This application claims benefit of Provisional Application No. 60/267,593 filed Feb. 8, 2001. The entire disclosure of Provisional Application No. 60/267,593 is hereby incorporated by reference herein for all purposes.

STATEMENT REGARDING FEDERALLY SPONSORED RESEARCH OR DEVELOPMENT

This invention was made with United States government support under Contract No. DAMD 17-01-C-0022 awarded by the Department of the Army. The United States government has certain rights in the invention.

BACKGROUND OF THE INVENTION

This invention relates to a skin patch including a telesensor, and particularly to a skin patch that includes a temperature sensor.

As used herein, the term "telesensor" means a device that allows a physiological parameter to be monitored at a distance and "temperature sensor" means a telesensor for which the physiological quantity is body temperature. A temperature sensor includes an element whose behavior depends substantially on temperature of the element and that emits a signal from which the temperature of the element can be derived.

Skin patches have been proposed for several purposes. One type of skin patch has been used to collect small quantities of perspiration in an absorbent pad. After the monitoring period, the patch can be removed from the subject's skin and the perspiration recovered from the absorbent pad. Through analysis of the perspiration, the presence and amount of various chemical species can be determined. For example, U.S. Pat. No. 4,329,999 (Philips) describes a skin patch useful for drug or alcohol detection. Skin patches have also been proposed in which chemically active strips are employed instead of absorbent pads. The strips react to specific chemicals of interest. For example, U.S. Pat. No. 4,444,193 (Fogt et al) discloses a skin patch in which two concentric circular reaction areas of chemically treated absorbent paper reactive to chloride in the perspiration are used for indicating cystic fibrosis. U.S. Pat. No. 4,732,153 (Philips) discloses a skin patch containing an active medium such as charcoal, which traps the perspiration and retains it during the monitoring period. After monitoring, the active medium is recovered and analyzed for the presence and amount of the chemical of interest. Skin patches having multiple test zones containing different respective active media, for collection and detection of different chemical species, have also been proposed.

Skin patches for administering chemicals transdermally have also been proposed. Skin patches have been developed to administer medications for pain relief and for hormonal and other replacement therapies.

SUMMARY OF THE INVENTION

In accordance with the invention there is provided a skin patch comprising a first layer of material, the first layer having first and second opposite main faces and the first main face having a coating of skin-compatible adhesive material, a second layer of material, the second layer having first and second opposite main faces and the first main face of the second layer being in confronting relationship with the second main face of the first layer, and a telesensor for emitting a signal that represents a physiological parameter sensed by the telesensor, the telesensor being sandwiched between the first and second layers.

BRIEF DESCRIPTION OF THE DRAWINGS

For a better understanding of the invention, and to show how the same may be carried into effect, reference will now be made, by way of example, to the accompanying drawings, in which FIG. 1 shows the patch with the cover layer removed and illustrates the layout of the components of the temperature sensor.

DETAILED DESCRIPTION

Figure 1:
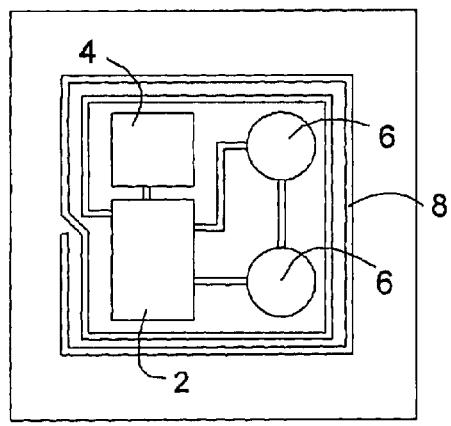
FIG. 1 is a top plan view of a first skin patch in accordance with the present invention; the telesensor is a temperature sensor
Figure 2:
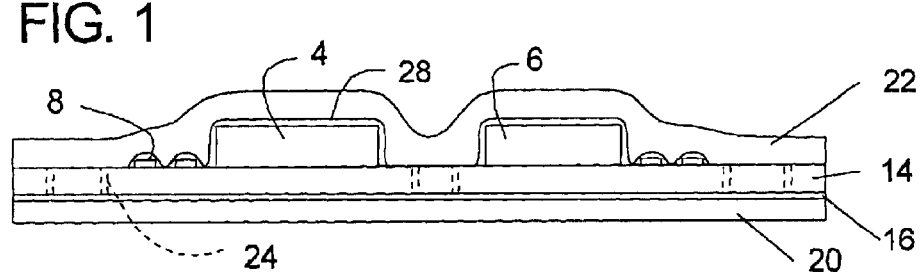
FIG. 2 is a schematic sectional view of the skin patch that is shown in FIG. 1.
Figure 3:
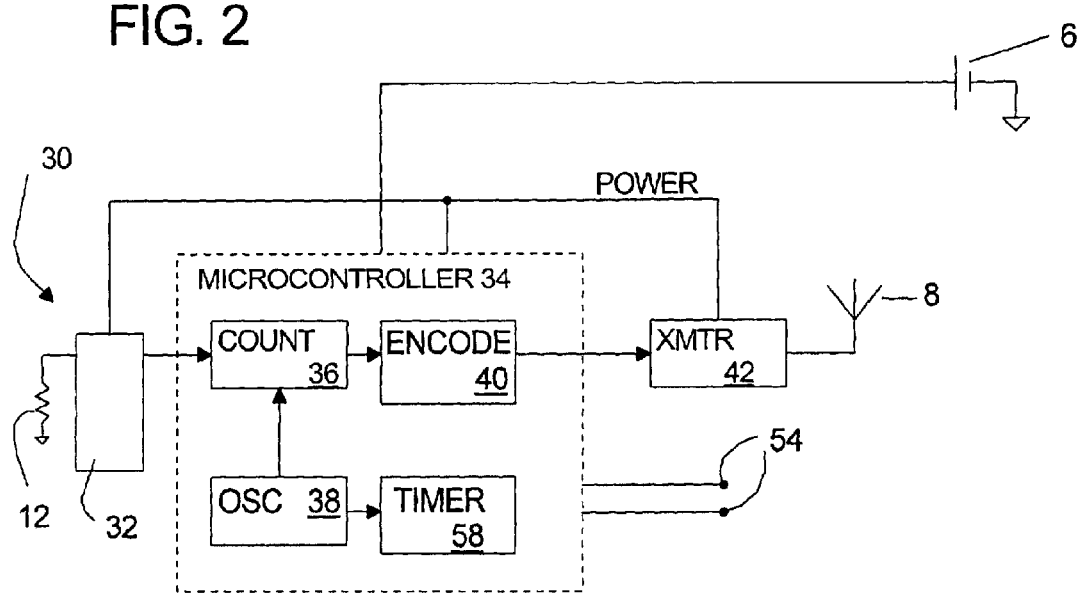
FIG. 3 is a schematic block diagram of the temperature sensor included in the skin patch shown in FIG. 1.

The skin patch shown in FIGS. 1–3 includes two integrated circuit chips 2, 4, two button cell batteries 6 connected to power supply terminals of the chip 2, and an antenna 8 connected to an output terminal of the chip 2. The integrated circuit chip 4 is connected to a thermistor 12 (FIG. 3) and several passive components (not shown). The electrical resistance of the thermistor 12 depends substantially on its temperature.

The button cells 6 are small and of relatively low profile and are of the type that are commonly used for hearing aids. The integrated circuit chips 2, 4 and associated components, the button cell batteries 6 and the antenna 8 form a temperature sensor. The temperature sensor, when active, periodically measures the temperature of the thermistor and then transmits the measurement information via an RF link. A receiving unit receives the transmission and derives the temperature.

The chips 2, 4, the batteries 6 and the antenna 8 are attached to an electrically insulating flexible circuit substrate 14, as are all other electrical components of the sensor. The flexible circuit substrate is provided on its undersurface with a coating 16 of an adhesive material. A removable protective layer 20 of paper adheres to the adhesive coating 16. The skin patch further includes a top or outer protective layer 22 of thermally insulating material over the temperature sensor and adhesively bonded to a peripheral margin of the flexible circuit substrate 14.

In use of the skin patch, the paper layer 20 is removed to expose the adhesive coating 16 and the patch is applied to the skin of a subject. The thermistor temperature equilibrates with skin temperature of the subject. The temperature sensor, if active, measures the temperature of the thermistor and transmits the temperature information.

In order for the skin patch to be physiologically compatible with the subject, the material of the adhesive coating should be one that can remain in contact with the skin for an extended period of time, e.g. four to five days, without causing an unacceptable reaction.

For a normal activity level, moisture transpires through the skin of a human subject at a moisture vapor transmission rate (MVTR) of about 425 $g/m^2$ per 24 hours. Vigorous exercise produces a higher MVTR while more sedentary behavior results in a lower MVTR. Moisture that transpires through the skin of a human subject may adversely affect the electrical components of the skin patch, i.e. the integrated circuit chips, the cells and the antenna, and accordingly it is desirable to protect these components from exposure to such moisture. The flexible circuit substrate generally has a very low MVTR capacity, so that if the flexible circuit substrate were imperforate, moisture would not permeate through the substrate and affect the electrical components. However, it is not desirable that moisture should be trapped in contact with the skin and therefore the skin patch must provide at least sufficient MVTR capacity for normal activity. This requirement necessitates that each layer of the skin patch have an MVTR capacity of at least 425 g/m$^2$ per 24 hours. Moreover, the upper layer must in addition be resistant to liquid water exposure. A number of commercially available materials have sufficient MVTR capacity and are resistant to liquid water.

Referring to FIG. 1, the patch is sufficiently large, and the electrical components are sufficiently small, that a substantial proportion of the area of the flexible circuit substrate 14 is not occupied by the electrical components. Several holes 24 through the substrate allow moisture to pass through the substrate. The holes 24 may be spaced away from the more sensitive electrical components.

Moisture that passes through the holes 22 in the substrate and enters the upper layer 22 will tend to permeate the entire upper layer. A water impermeable and electrically insulating conformal coating 28 of a polyurethane or epoxy material is provided over the electrical components in order to protect them from corrosion and humidity effects due to moisture present in the upper layer.

Referring to FIG. 3, the integrated circuit chip 4 implements a timer 32, and the timer 32, the thermistor 12 and passive components implement an astable multivibrator 30. The astable multivibrator 30 generates a periodic output signal in the form of a square wave having a duty cycle that depends on the resistance of the thermistor 12. The output signal of the multivibrator 30 is supplied to a microcontroller 34 implemented in the integrated circuit chip 2. The microcontroller includes a counter 36, which uses a clock signal generated by an oscillator 38 to measure the length of time in each cycle of the output signal of the multivibrator for which the output signal is in the logic high state and the length of time for which the output signal is in the logic low state, and calculates the ratio of these times. Since the duty cycle of the output signal depends on the temperature of the thermistor 12, this ratio also depends on the temperature of the thermistor. The ratio is encoded by an encoder 40 as a component of a digital transmission packet. The encoder supplies the digital transmission packet to a radio transmitter 42 which is also implemented in the chip 2 and uses the transmission packet to modulate a carrier and the modulated carrier drives the antenna 8 for radiating the signal.

The skin patch is used in conjunction with a receiving unit (not shown) which includes an antenna for receiving the signal radiated by the transmitting antenna 8, an amplifier for amplifying the received signal, a microcontroller for decoding the received signal and recovering the ratio value and calculating temperature based on the ratio value, a memory for storing calculated temperature values, and a readout device for displaying the calculated temperature values.

In order to prolong shelf life and operating life of the skin patch, the microcontroller controls supply of power to the multivibrator 30 and the transmitter 42. The microcontroller 34 further controls its own power consumption by use of low-power sleep and suspend modes.

The microcontroller 34 is initially activated to its normal active mode by applying a specific signal sequence to contact pads 54, which are exposed on the paper layer and are connected to the microcontroller through vias that pass through the flexible circuit substrate and the paper layer 20. In the normal mode, the multivibrator and transmitter are powered. When the microcontroller has been activated, it periodically returns to and exits from the suspend mode. In the suspend mode of the microcontroller, the multivibrator and transmitter are not powered.

When the skin patch is first assembled, the microcontroller enters a calibration mode and then enters the low-power sleep mode. In the sleep mode, the multivibrator and the transmitter are not powered. From this time until the skin patch is activated, the only power consumed is that which is required to maintain the microcontroller in the sleep mode. When the device is to be put to use, an activator circuit, which may be incorporated in the receiving unit, applies the wake-up signal sequence to the contact pads 54. If the proper wake-up signal sequence is detected by the microcontroller, the microcontroller enters the normal operating mode, in which it supplies operating current to the multivibrator and the transmitter for measuring temperature and transmitting temperature information. The active mode alternates with the stand-by mode to conserve power when not measuring or transmitting.

When the microcontroller detects the proper wake-up signal sequence, it also powers the multivibrator and the transmitter in order to measure the temperature, as sensed by the thermistor, and send a short repeated sequence of measurement data, which includes a unique identifier for the temperature sensor. This data, transmitted using the antenna 8, is interpreted by the receiving unit, which provides the user with an indicator that successful activation has been achieved. The user can then disconnect the skin patch from the activation circuit. The paper layer is then removed, thereby also removing the contact pads 54 and effectively rendering the activation terminals of the microcontroller inaccessible. The patch is ready to be applied to the subject's skin.

After transmitting the measurement and identification data, the microcontroller removes power from the multivibrator and transmitter 42 and enters the standby mode. While in this standby mode, a timer 58 in the microcontroller continues timekeeping functions and after a predetermined interval wakes the microcontroller into active mode. The microcontroller activates the circuits when appropriate and performs the operations described above in connection with measuring the ratio and transmitting the encoded data. The microcontroller then removes power, re-enters the standby mode, and repeats the cycle.

Further details regarding the operation of the temperature sensor are disclosed in U.S. Pat. No. 6,629,776, the entire disclosure of which is hereby incorporated by reference herein for all purposes.

Figure 4:
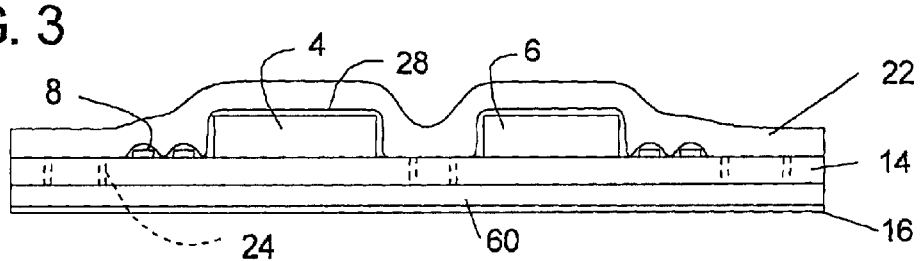
FIG. 4 is a schematic sectional view of a second skin patch in accordance with the present invention.

FIG. 4 illustrates a modification of the skin patch described with reference to FIGS. 1–3. In accordance with FIG. 4, the coating of physiologically compatible adhesive material is not provided on the undersurface of the flexible circuit substrate. The skin patch includes an additional layer 60 adhesively bonded to the undersurface of the flexible circuit substrate 14 and the adhesive coating 16 is provided on the undersurface of the layer 60. The layer 60 is made of a material having an MVTR capacity of at least 425 g/m$^2$ per 24 hours.

It will be appreciated that the invention is not restricted to the particular embodiment that has been described, and that variations may be made therein without departing from the scope of the invention as defined in the appended claims and equivalents thereof. For example, in one alternative embodiment the microcontroller may be activated by transmitting the wake-up signal sequence from the activation unit optically instead of electrically. Further, it would be possible to provide sufficient memory in the temperature sensor to record temperature measurements over several days, in which case the stored data could be retrieved after the measurement period and it might not be necessary to include a transmitter and an antenna in the temperature sensor. Although the invention has been described with reference to a temperature sensor, the invention is also applicable to other telesensors, for example telesensors that emit signals representative of heart rate, heart rate interbeat interval, activity level, including activity level at the sensor location, and blood oxygen level. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated.

What is claimed is:

1. A skin patch comprising:
   a first layer of material, the first layer having first and second opposite main faces and the first main face having a coating of skin-compatible adhesive material,
   a second layer of material, the second layer having first and second opposite main faces and the first main face of the second layer being in confronting relationship with the second main face of the first layer, and
   a telesensor for emitting a signal that represents a physiological parameter sensed by the telesensor, the telesensor being sandwiched between the first and second layers,
   and wherein the first and second layers are permeable to water vapor.

2. A skin patch according to claim 1, wherein the first layer is a flexible circuit substrate of electrically insulating material and the telesensor is attached to the flexible circuit substrate.

3. A skin patch according to claim 2, wherein the flexible circuit substrate is formed with through holes spaced from the telesensor.

4. A skin patch according to claim 3, wherein the telesensor includes at least one electrical component attached to the flexible circuit substrate, and wherein the holes are spaced from said electrical component.

5. A skin patch according to claim 1, wherein the telesensor is a temperature sensor that includes an astable multivibrator incorporating a thermistor, the astable multivibrator generating a square wave output signal having a duty cycle that depends on the temperature of the thermistor, and the temperature sensor further comprises a microcontroller that receives the output signal of the multivibrator and generates said temperature signal.

6. A skin patch according to claim 5, wherein the temperature sensor further includes a radio transmitter connected to the microcontroller for receiving the temperature signal and encoding a carrier signal with the temperature signal, and an antenna for radiating the encoded carrier signal.

7. A skin patch according to claim 6, wherein the temperature sensor includes a means for encoding the carrier signal with identifying information.

8. A skin patch according to claim 1, including a flexible circuit substrate having first and second opposite main faces, the first main face of the flexible circuit substrate being in confronting relationship with the second main face of said first layer and the second main face of the flexible circuit substrate being in confronting relationship with the first main face of the second layer, and wherein the telesensor is attached to the flexible circuit substrate at the second main face thereof.

9. A skin patch according to claim 1, wherein the second layer is a conformal coating over the telesensor.

10. A skin patch according to claim 1, wherein the second layer is permeable to water vapor at its first face and is impermeable to liquid water at its second face.

11. A skin patch according to claim 10, further comprising a conformal coating of electrically insulating and water impermeable material over the telesensor.

12. A skin patch according to claim 10, wherein the telesensor is a temperature sensor and the second layer is made of a thermally insulating material.

13. A skin patch comprising:
   a perforated flexible circuit substrate having first and second opposite main faces and the first main face having a coating of skin-compatible adhesive material,
   a layer of material having a moisture vapor transmission rate of at least 425 g/m$^2$ per 24 hours, said layer having first and second opposite main faces and the first main face of said layer being in confronting relationship with the second main face of the flexible circuit substrate, and
   a telesensor for emitting a signal that represents a physiological parameter sensed by the telesensor, the telesensor being attached to the flexible circuit substrate and covered by said layer.

14. A skin patch according to claim 13, wherein the telesensor includes at least one electrical component attached to the flexible circuit substrate and the perforations in the flexible circuit substrate are spaced from said electrical component.

15. A skin patch according to claim 13, wherein the telesensor includes at least one electrical component attached to the flexible circuit substrate and the skin patch further comprises a conformal coating of water impermeable material over the electrical component.

16. A skin patch according to claim 13, wherein said layer is permeable to water vapor at its first face and is impermeable to liquid water at its second face.

17. A skin patch according to claim 13, further comprising a conformal coating of electrically insulating and water impermeable material over the telesensor.

18. A skin patch comprising:
   a first layer of material, the first layer having first and second opposite main faces and the first main face having a coating of skin-compatible adhesive material,
   a second layer of material, the second layer having first and second opposite main faces and the first main face of the second layer being in confronting relationship with the second main face of the first layer,
   a perforated flexible circuit substrate having first and secon opposite main faces, the first main face of the flexible circuit substrate being in confronting relationship with the second main face of said first layer and the second main face of the flexible circuit substrate being in confronting relationship with the first main face of the second layer, and
   a telesensor for emitting a signal that represents a physiological parameter sensed by the telesensor, the telesensor being attached to the flexible circuit substrate at the second main face thereof, and wherein the first and second layers are permeable to water vapor.

19. A skin patch according to claim 18, wherein the telesensor includes at least one electrical component attached to the flexible circuit substrate are spaced from said electrical component.

20. A skin patch according to claim 18, wherein the telesensor includes at least one electrical component attached to the flexible circuit substrate and the skin patch further comprises a conformal coating of water impermeable material over the electrical component.

21. A skin patch according to claim 18, wherein the second layer is made of a material that is permeable to water vapor at its first face and is impermeable to liquid water at its second face.

22. A skin patch according to claim 18, further comprising a conformal coating of electrically insulating and water impermeable material over the telesensor.

23. A skin patch according to claim 18, wherein the first and second layers each have a moisture vapor transmission rate of at least 425 $g/m^2$ per 24 hours.

* * * * *

UNITED STATES PATENT AND TRADEMARK OFFICE
CERTIFICATE OF CORRECTION

PATENT NO. : 6,814,706 B2
DATED : November 9, 2004
INVENTOR(S) : Donna K. Barton et al.

It is certified that error appears in the above-identified patent and that said Letters Patent is hereby corrected as shown below:

Column 6,
Line 60, "secon" should be deleted and replaced with -- second --.

Column 7,
Line 7, -- and the perforations in the flexible circuit substrate -- should be inserted after "substrate".

Signed and Sealed this

Nineteenth Day of April, 2005

JON W. DUDAS
*Director of the United States Patent and Trademark Office*